United States Patent [19]
Medoff

[11] Patent Number: 6,113,603
[45] Date of Patent: Sep. 5, 2000

[54] GRAFT CONSTRAINT DEVICE

[76] Inventor: Robert J. Medoff, 159 Ku'Ukama St., Kailua, Hi. 96734

[21] Appl. No.: 09/180,161
[22] PCT Filed: May 6, 1997
[86] PCT No.: PCT/SE97/00749
   § 371 Date: Apr. 26, 1999
   § 102(e) Date: Apr. 26, 1999
[87] PCT Pub. No.: WO97/42912
   PCT Pub. Date: Nov. 20, 1997

[30]   Foreign Application Priority Data

May 10, 1996  [SE]  Sweden .................................. 9601783

[51] Int. Cl.⁷ ............................... A61F 2/28; A61B 17/80
[52] U.S. Cl. ................................................. 606/69; 623/16
[58] Field of Search ........................... 606/69, 70; 623/16

[56]   References Cited

U.S. PATENT DOCUMENTS

| | | | |
|---|---|---|---|
| 3,710,789 | 1/1973 | Ersek | 606/69 |
| 4,503,848 | 3/1985 | Caspar et al. | 606/69 |
| 4,651,724 | 3/1987 | Berentry et al. | 606/69 |
| 4,865,603 | 9/1989 | Noiles | 623/16 |
| 4,867,144 | 9/1989 | Karas et al. | 606/69 |
| 5,015,248 | 5/1991 | Burstrin et al. | 606/69 |
| 5,344,421 | 9/1994 | Crook | 606/70 |
| 5,380,328 | 1/1995 | Morgan | 606/70 |
| 5,468,242 | 11/1995 | Reisberg | 606/69 |
| 5,507,815 | 4/1996 | Wagner et al. | 623/16 |
| 5,586,985 | 12/1996 | Putnam et al. | 606/69 |
| 5,718,704 | 2/1998 | Medoff | 606/69 |
| 5,730,743 | 3/1998 | Kirsch | 606/69 |
| 5,741,257 | 4/1998 | Kirsch | 606/69 |
| 5,743,913 | 4/1998 | Wellisz | 606/69 |
| 5,766,176 | 6/1998 | Duncan | 606/69 |
| 5,797,916 | 8/1998 | McDonell | 606/69 |
| 5,814,048 | 9/1998 | Morgan | 606/69 |

FOREIGN PATENT DOCUMENTS

| | | |
|---|---|---|
| 0609738 | 8/1994 | European Pat. Off. . |
| 2721195 | 12/1995 | France . |
| 601851 | 11/1985 | U.S.S.R. . |
| 9614802 | 5/1996 | WIPO . |

OTHER PUBLICATIONS

Abstract of SU 601851 of Nov. 1985, *Derwent Publications LTD*. No. 86–111257/17.

*Primary Examiner*—Paul J. Hirsch
*Attorney, Agent, or Firm*—Ladas & Parry

[57]   ABSTRACT

The present invention relates to a graft constraint device (10), having the main object of constraining graft material (1) packed into a bone defect or a space for buttressing an adjacent bone fragment, the graft material being autologous bone, allograft bone, xenograft, organic or inorganic material, "bone paste" or other similar materials. The graft constraint device (10) has a constraint end (12) and a fastening end (13), at which the device (10) is applied to a stable bone cortex with suitable fasteners (11).

14 Claims, 2 Drawing Sheets

GRAFT CONSTRAINT DEVICE

FIELD OF THE INVENTION

The present invention relates to a means for constraining graft material.

BACKGROUND

Grafting materials, such as autologous bone, allograft bone, xenograft, organic or inorganic material or "bone paste", or other similar materials, are commonly used in procedures for fractures or surgical reconstruction of bones. These materials are used for two primary reasons—(1) in order to promote bone healing as a biologic response, and (2) in order to provide structural support.

Intraarticular fractures are a common example of a situation in which grafting material can be used. In this situation, the primary role of the grafting material is to buttress and/or support bone fragments in an anatomic or functional position; in addition, the graft material may function to promote healing.

If the grafting material does not maintain its position at the site of application, several potential problems may occur. First and foremost is that the material no longer functions for its original and intended purpose. Migration of graft material may lead to migration of the fragment to be supported; this in turn may result in complications of joint incongruity, arthritis, stiffness, pain, crepitance with joint motion, nonunion or malunion, and secondary procedures (i.e. additional surgical procedures), to name a few.

In addition to losing intended function, migration of graft material may have additional deleterious effects. Migration of grafting material into adjacent soft tissues may initiate an inflammatory reaction or cause complications from mechanical pressure and irritation. For instance, graft material pressing on a nerve may cause nerve damage. Graft material pressing on tendons may cause either fraying of the tendon (even rupture) or may cause scarring and limitation of tendon gliding. Migration of graft material into an adjacent joint can cause arthritis and joint damage. Moreover, the ability of grafting material to stimulate bone formation may cause problems if the graft migrates into the soft tissues. Occasionally, this may even stimulate formation of heterotopic bone in the soft tissues, which can cause scarring, stiffness, inflammation and pain.

SUMMARY OF THE INVENTION

The present invention addresses these problems by constraining the graft material at the site of application. For instance, one example of the present invention is to constrain graft material used with a comminuted Colles' fracture. By maintaining the graft material at the original site of application, this invention avoids the complications association with migration or drift of the graft material.

Thus, there is a need for a means to constrain graft material in its intended position and to hinder the graft material from migration. This need is met by a device according to the invention having one end for constraining the graft material and an opposite end for receiving a fastening means for attachment to stable bone cortex.

BRIEF DESCRIPTION OF THE DRAWINGS

The present invention will now be described in greater detail hereinbelow, with the aid of embodiments shown in the drawings wherein.

DETAILED DESCRIPTION

In this description the expression "constraining end" is used to indicate the part of the graft constraint device which actually constrains the graft material. The expression "fastening end" is used to indicate the part of the graft constraint device which receives the fastening means for securing the device to a stable bone cortex.

Figure 1:
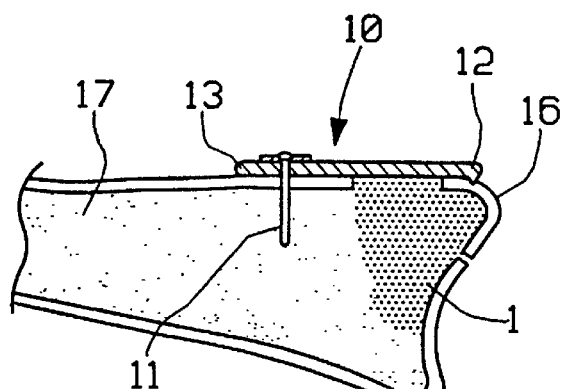
FIG. 1 is a side sectional view, taken on line 1—1 in FIG. 2 of a first embodiment of the invention, applied on the radius.
Figure 2:
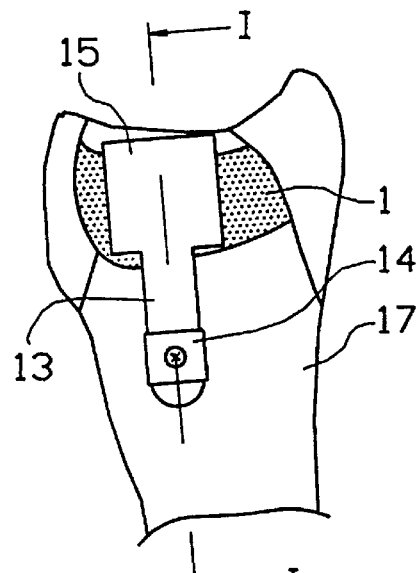
FIG. 2 is a top view, of the embodiment of FIG. 1

The first embodiment of the invention shown in FIGS. 1 and 2 consists of a graft constraint device 10 having one constraining end 12 and one fastening end 13. The graft constraint device 10 is applied to a stable bone cortex of the radius 17 with fastening means. In this embodiment the fastening means is a screw 11 and a washer 14. In other embodiments the fastening means is only a screw, i.e. no washer is needed. The constraining end 12 of the graft constraint device 10 is formed into a plate 15 covering the opening into which the graft material 1 is inserted. In this embodiment and as viewed in FIG. 2 the plate 15 is broader than the fastening end 13. The size and design of the plate 15 is determined based on the conditions at the actual site of application, such as the positions and sizes of the fractures and fragments. Thus, in some embodiments the plate 15 may have the same width or even be narrower than the fastening end 13. At the outer end of the plate 15 pointed projections 16 are furnished for engagement with bone cortex. In another embodiment (not shown) the plate has no pointed projections. The graft constraint device 10 is secured to the radius 17 after the graft material has been placed. In a further embodiment (not shown) the plate has the form of a mesh or is furnished with multiple openings to allow ingrowth of blood vessels in the graft material.

Figure 3:
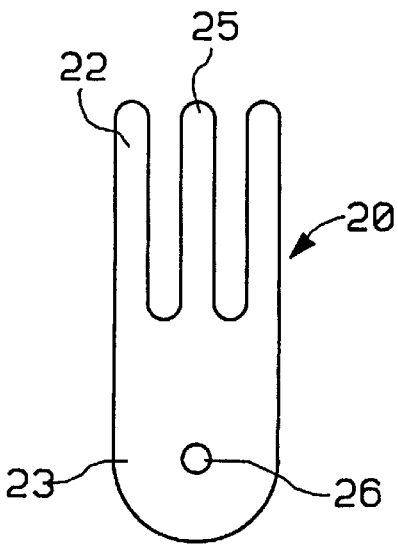
FIG. 3 is a top view, of a second embodiment of the invention.

Also in the second embodiment, shown in FIG. 3, the graft constraint device 20 has a fastening end 23 and a constraining end 22. The fastening end 23 is similar to the fastening end 13 of the first embodiment and has an opening 26 for receiving a fastening means. The constraining end 22 comprises malleable fingers 25, which allow contouring to the uneven anatomical site of application. The openings between the fingers 25 allow ingrowth of blood vessels into the grafting material.

Figure 4:
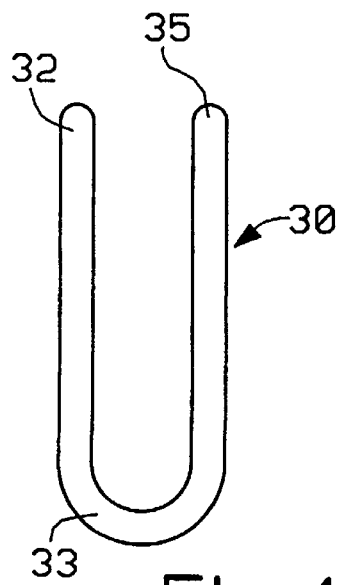
FIG. 4 is a top view, of a third embodiment of the invention.

In the third embodiment, shown in FIG. 4, the graft constraint device 30 is a wire bent into a U-shape. The diameter of the wire is preferably between 0.010" to 0.250". The base of the "U" forms the fastening end 33 and the upper part of the "fingers" 35 of the "U" forms the constraining end 32. This graft constraint device 30 is fastened at stable bone cortex by means of a screw 11 and washer 14. Also this embodiment is malleable enough to allow contouring to the actual site of application and allow ingrowth of blood vessels into the grafting material 1.

As an option, pointed projections cooperating with bone cortex are furnished at the outer ends of the fingers 35 of the graft constraint device 30 made of a wire bent into a U-shape. The pointed projections may be formed by bending the outer part of the wires 35. The site of the bend decides how far into, or even through, the graft the projections will go.

Figure 7:
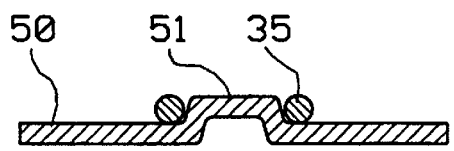
FIGS. 7 and 8 are cross-section views of optional plates used with the invention.
Figure 8:
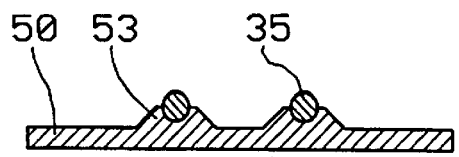

As a further option a small plate (FIGS. 7, 8) is placed between the extraosseous surface of the radius and the fingers 35 of the U. In this way the load of the graft constraint device is spread over a wider area. In its most simple embodiment the plate 50 is a simple straight plate. In further embodiments the plate is furnished with means to constrain the plate from migrating. The means to constrain the plate from migrating may have any suitable form such as the plate having a raised area 51 between the fingers 35 of the U, forming two seats 52 for receiving the fingers 35 of the U, or having two small holes placed near the distal edge of the plate to allow passage for the pointed projections of the bent fingers 35 of the U. If needed said plate is bent to conform to the dorsal surface.

Figure 5:
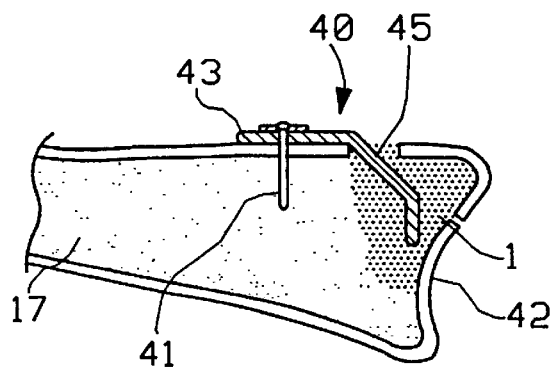
FIG. 5 is a side sectional view, taken on line V—V in FIG. 6 of a fourth embodiment of the invention, applied on the radius.
Figure 6:
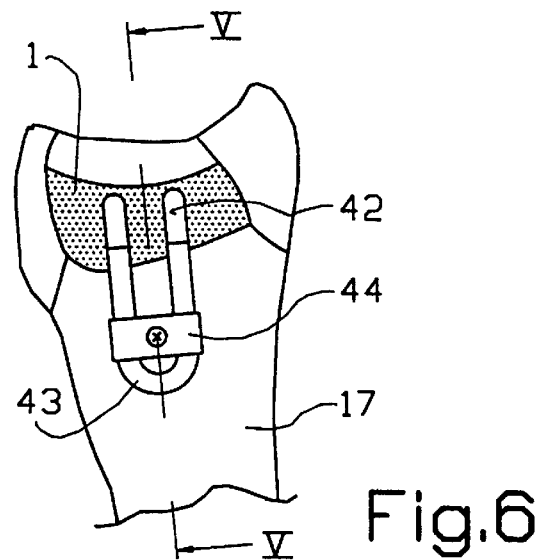
FIG. 6 is a top view, of the embodiment in FIG. 5.

The fourth embodiment shown in FIGS. 5 and 6 is especially intended for use with synthetic graft materials. One example of such material is synthetic "bone paste" made by Norian Corp. The bone paste is injected into the osseous defect and allowed to harden. A graft constraint device according to the previous embodiments would constrain the material, but would not prevent the graft material from displacing proximally within the bone itself. The graft constraint device 40 according to this embodiment is U-shaped with the base of the "U" forming the fastening end 43. The fastening end 43 receives a screw 41 and washer 44 for securing the device to stable bone cortex. The constraint end 42 of the device 40 has the form of fingers 45 bent downward to project into the graft material 1. In use the fingers 45 are placed in the graft material while it is still soft. Then the synthetic graft material is allowed to harden around the fingers 45 projecting into the graft material.

In further embodiments (not shown) the constraining end is a combination of the above embodiment and one of the previous embodiments. Thus, it has several "fingers" of which at least one projects into the graft material and at least one lies over the graft material.

The graft constraint device is made thin and may in some embodiments be formed to follow the contour of the site of application, to minimize any discomfort for the patient. The graft constraint device is unobtrusive to avoid irritation of the adjacent soft tissue.

A person skilled in the art realizes that the graft constraint device, at the same time as being soft enough to contour, has sufficient stiffness for its intended purpose as a buttress.

In the embodiments shown in the figures screws with or without washers are used as fastening means. A person skilled in the art perceives that other fastening means may be used. Thus, in other embodiments pins, wires, blades, staples, brackets or indirect coaption with another device scurely attached to the stable bone is used instead of screws to apply the device to a stable bone cortex.

As an option, pointed projections cooperating with bone cortex are furnishedat the constraining end 12,22,32,42 of the graft constraint device 10,20,30,40 according to the different embodiments. The form of these pointed projections varies in that they may be pointed or not, and may be long enough to pass through a hole placed in the graft, such as a small hole drilled through a piece of cortical bone graft. Such an application would further constrain the graft material from slipping under the device.

The above description has referred to but a limited number of embodiments of the present invention, but it will be readily perceived by a person skilled in the art that the present invention encompasses a large number of embodiments without departing from the spirit and scope of the appended claims.

What is claimed is:

1. A device for constraining graft material packed into a bone defect or a space for buttressing an adjacent bone fragment, said device comprising a graft restraining member having one end with means for constraining the graft material and an opposite end for receiving fastening means for securing the graft restraining member to a stable bone cortex, said graft material comprising a hardenable synthetic material, said means for constraining the graft material being applied as a buttress for containing the synthetic graft material after said synthetic graft material hardens, said means for constraining said synthetic graft material including projecting members inserted into said synthetic graft material before said synthetic graft material hardens so that after said synthetic graft material hardens, said projecting members become integral with said synthetic graft material to hold the hardened graft material in position and prevent translation movement thereof.

2. The device of claim 1, wherein said one end of said graft restraining member for constraining the graft is malleable ti allow contouring of said projecting members to be adapted to its site of application.

3. The device of claim 1, wherein said one end of said graft restraining member has at least one opening to allow ingrowth of blood vessels.

4. The device of claim 1, wherein said means at said one end of the graft restraining member further comprises a buttressing plate covering at least a part of the graft material.

5. The device of claim 1, wherein said means at said one end of the graft restraining member further comprises a mesh.

6. The device of claim 1, wherein said projecting members comprises a plurality of malleable fingers.

7. The device of claim 1, wherein said graft restraining member comprises a wire bent into U-shape.

8. The device of claim 1, further comprising a plate for placement between the graft restraining member and underlying bone at said one end of the graft restraining member.

9. The device of claim 8, wherein said plate includes seats for receiving said graft restraining member.

10. The device of claim 9, wherein said plate includes a raised portion forming said seats.

11. The device of claim 1, wherein said graft restraining member at said one end includes a portion for covering the graft material and from which said projecting members extend into the graft material.

12. The device of claim 1, wherein said fastening means comprises a screw.

13. The device of claim 6, wherein said synthetic graft material is packed into the bone defect or space to a determined depth and said fingers project into said synthetic graft material over a substantial portion of the depth of said graft material.

14. The combination of said device and said synthetic graft material as claimed in claim 1.

* * * * *